United States Patent [19]

Stangerup

[11] Patent Number: 5,546,964
[45] Date of Patent: Aug. 20, 1996

[54] METHOD FOR TREATING A BLEEDING NOSE

[76] Inventor: Sven-Eric Stangerup, Slettebjerget 83, DK-3400 Hillerød, Denmark

[21] Appl. No.: 379,151

[22] Filed: Jan. 27, 1995

[30] Foreign Application Priority Data

Feb. 2, 1994 [SE] Sweden .................... 9400364

[51] Int. Cl.⁶ ........................................ A61B 17/12
[52] U.S. Cl. ................................. 128/898; 606/196
[58] Field of Search .................... 128/897, 898; 606/196, 199

[56] References Cited

U.S. PATENT DOCUMENTS

| 2,493,326 | 1/1950 | Trinder | 606/196 |
| 4,338,941 | 7/1982 | Payton | 606/196 |
| 4,883,465 | 11/1989 | Brennan | 606/199 X |

FOREIGN PATENT DOCUMENTS 1806641  4/1993  U.S.S.R. ................... 606/199

Primary Examiner—Angela D. Sykes
Assistant Examiner—Samuel Gilbert
Attorney, Agent, or Firm—Brumbaugh, Graves, Donohue & Raymond

[57] ABSTRACT

The present invention relates to a method for treating nosebleed using warm water rinse, whereby a catheter having an inflatable balloon in its front end and having an opening immediately below said balloon for the administration of a liquid, preferably an aqueous liquid, is introduced into the nose cavity to a point beyond the bleeding point with regard to the balloon, the balloon is inflated and a rinsing liquid is introduced through said catheter for rinsing the nosebleed point for a time sufficient to inhibit the nosebleed.

4 Claims, 3 Drawing Sheets

METHOD FOR TREATING A BLEEDING NOSE

DESCRIPTION

TECHNICAL FIELD

The present invention relates to a method for treating a bleeding nose (epistaxis).

The object of the present invention is to obtain a possibility to treat epistaxis in a simple and rational way.

BACKGROUND OF THE INVENTION

Epistaxis is a highly common occurring illness, whereby 10% of the population at one or another time point will obtain a nosebleed that requires treatment. One normally differs between local and general causes, whereby these may be combined.

The local causes are, in particular trauma (inter alia nose picking), flebektasises (vein knots) at the front of septum, and perforations; more rarely are tumors involved.

The general causes are in particular arterosklerosis, by hyper-tension, different conditions with increased bleeding tendency, as well as cataractic infections (influenza).

From a treatment point of view it is practical to differ between bleeds from the front part of the nose (epistaxis anterior) and bleeds from the rear or lower parts of the nose (epistaxis posterior).

At epistaxis anterior the bleeding spot can be observed directly and the bleeding can be inhibited by means of clamping of the nose, etching, electrical coagulation or direct tamponing. Treatment of this type of nosebleed is as a rule, uncomplicated and relatively painless and the treatment can be carried out by the patient self, a doctor on his own or a nursing center. It is seldom that the condition requires hospitalization of the patient.

Epistaxis posterior is often present in older patients and is much more difficult to treat. Hospitalization is quite often necessary. The bleeding spot is often hidden and can thus not be treated directly. The nose cavity has to be stuffed up carefully, which is often very unpleasant to the patient. The nose cavity shall be stuffed in a hard way until the patient has been free of bleeding for at least 24 hrs. The average hospitalization time for patients suffering from epistaxis posterior is about 4 days, of which 3 days with nose tamponing. Besides the direct discomfort as a consequence of the tamponing of the nose (lack of breathing ability through the nose and pain), mucous membrane necrosis and sinuitis closure are not rarely occurring complications during tamponing of the nose.

It has previously been proposed to rinse the interior of the nose with warm water, whereby the patient sits with his head slightly bent forward. Using a large syringe (200 ml) arranged on a nose adapter which closes against the nostril, the bleeding side of the nose is rinsed using water having a temperature of 48° to 50° C. until the bleeding has ceased. During the rinsing the water flows backwards and down into the pharynx and finally out through the mouth.

The treatment using warm water at nosebleed was first described by N. L. Gluice in 1884, whereby the treatment also has been disclosed as a routine treatment at posterior epistaxis by Oscar Bloch in "Noter til kliniske forelaesningar" (Notes to clinical lessons) 1907. The last time the treatment was mentioned as a possible alternative was in "Nordisk laerebog i öre-näse-hals-sygdomme" (Nordic textbook in ear-nose-throut-illnesses) 1958. During the later years the rinsing using warm water has only seldom been used as a treatment of nosebleed.

At department for ear-nose-and-throut-illnesses of the Gentofte amt hospital a prospective, random investigation of the value of "warm water rinse" compared to tamponing was initiated. The result was very promising, and beside proved less pain using a warm water rinse compared to tamponing, the mean hospitalization time was considerably shorter. The investigation was, however, finished before the planned finish due to problem with lack of co-operation from the patients concerning the warm water treatment.

The substantial problem using the hitherto known method has been the troublesome flow of water through the mouth in combination with a perturbation of the upper air ways.

It shall also be mentioned that within the medical-technical field there is a catheter, the so called Foley-catheter, which has an inflatable balloon in its front end, which catheter has been used for emptying the urine bladder, whereby the urine flows out through the forward open end of the catheter and the balloon has the task of holding the catheter in the bladder.

It would therefore be desirable to create an improved method for carrying out the treatment of a nosebleed.

DESCRIPTION OF THE PRESENT INVENTION

It has now surprisingly turned out possible to be able to eliminate said known problems using the present method which is characterized in that a catheter having an inflatable balloon in its front end and having an opening immediately below said balloon for administration of a liquid, preferably an aqueous liquid, is introduced into the nose cavity to a point beyond the bleeding point with regard to the balloon, the balloon is inflated and a rinsing liquid is introduced through said catheter for rinsing the nosebleed point for a time sufficient to inhibit the nosebleed.

By means of the present invention the upper air ways of the rear parts of the nose cavity can be closed and a rinse using warm water can be carried out in the nose cavity as such.

The present invention will now be described in relation to the attached drawing, wherein FIG. 1 shows a lateral view of a catheter according to the invention, FIG. 2 shows the embodiment of FIG. 1 having an expanded balloon FIG. 3 shows the embodiment of FIG. 1 having an expanded balloon and during administration of warm water FIGS. 4a–4f shows different cross sections of the catheter of FIG. 2

Figure 1:
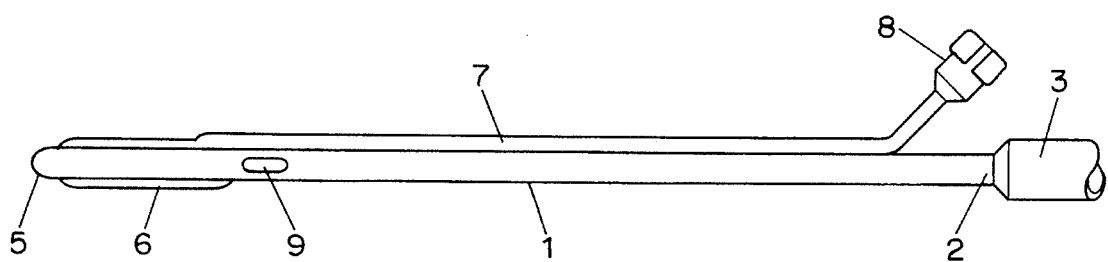
Figure 2:
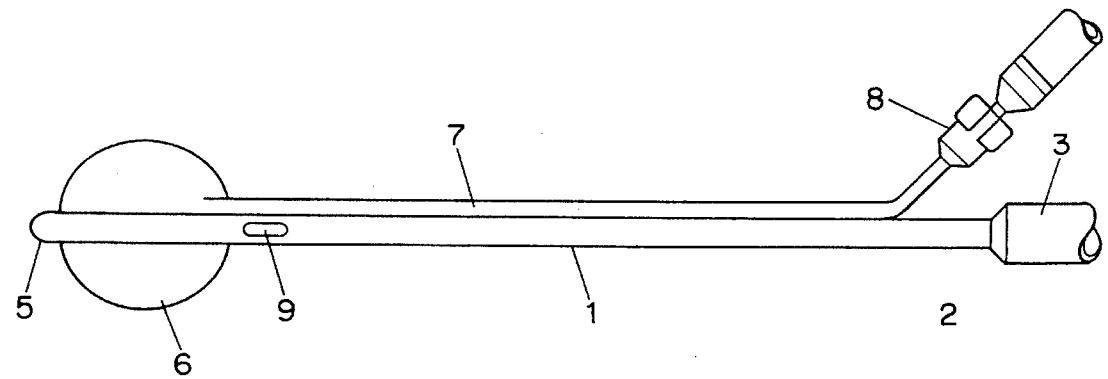
Figure 3:
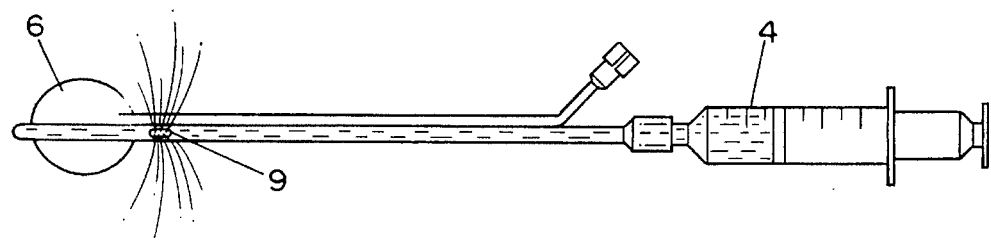
Figure 4:
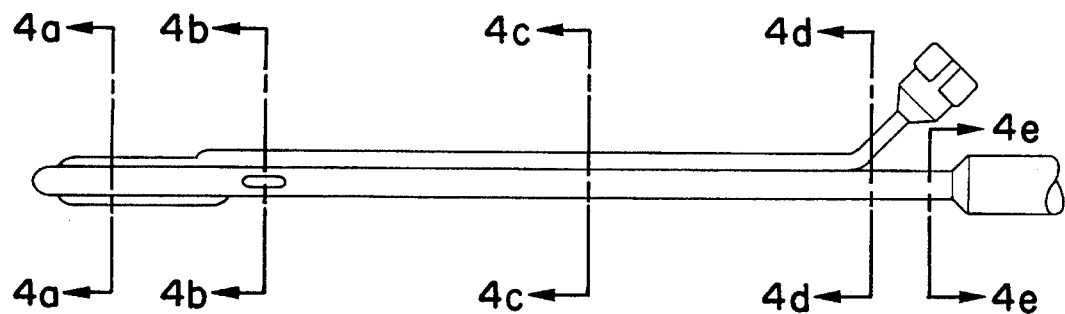
Figure 4A:
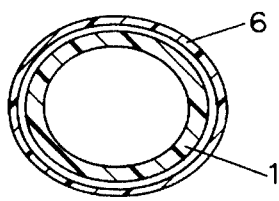
Figure 4B:
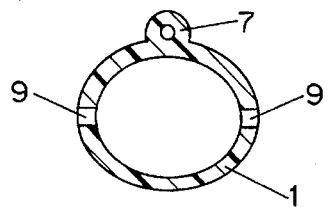
Figure 4C:
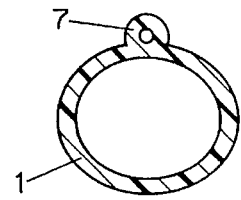
Figure 4D:
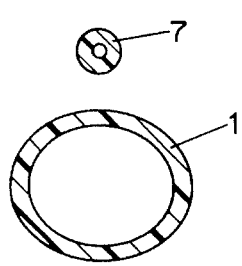
Figure 4E:
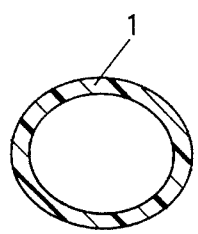
Figure 4F:
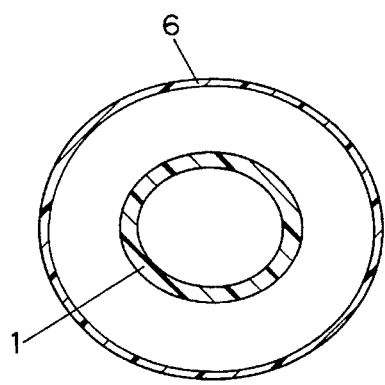

1 denotes in general a catheter tube on the rear end 2 of which an adapter 3 for receiving a syringe 4 or a similar object is arranged. The front end 5 of the catheter 1 is closed. Around the front end 5 a balloon 6 is present, which contains 5 to 15 ml, and which can be inflated by air or be filled with a liquid via a tube 7 applied, in the drawings, on the top side of the catheter, which tube is provided with an adapter 8 for air or liquid, which adapter 8 is separated from the catheter as such and which adapter 8 is provided with a self-closing material or a one-way valve. When a syringe, for air or liquid, is introduced in the adapter 8 the valve or the material will be opened and the air or liquid can inflate the balloon 6. Immediately beyond, underneath the balloon 6, towards the rear end 2 of the catheter 1, there is arranged at least one, preferably two to three throughgoing openings 9, which openings connect the inner of the catheter tube 1 with the outer side and through which tube 1 and openings 9 a liquid can be forced.

The catheter tube 1, which has a length of about 15 cm is prepared in a soft and flexible material, which preferably has been hydrophilized in order to be able to be introduced more easily in a nose cavity, over the moist mucous membranes.

Figure 5:
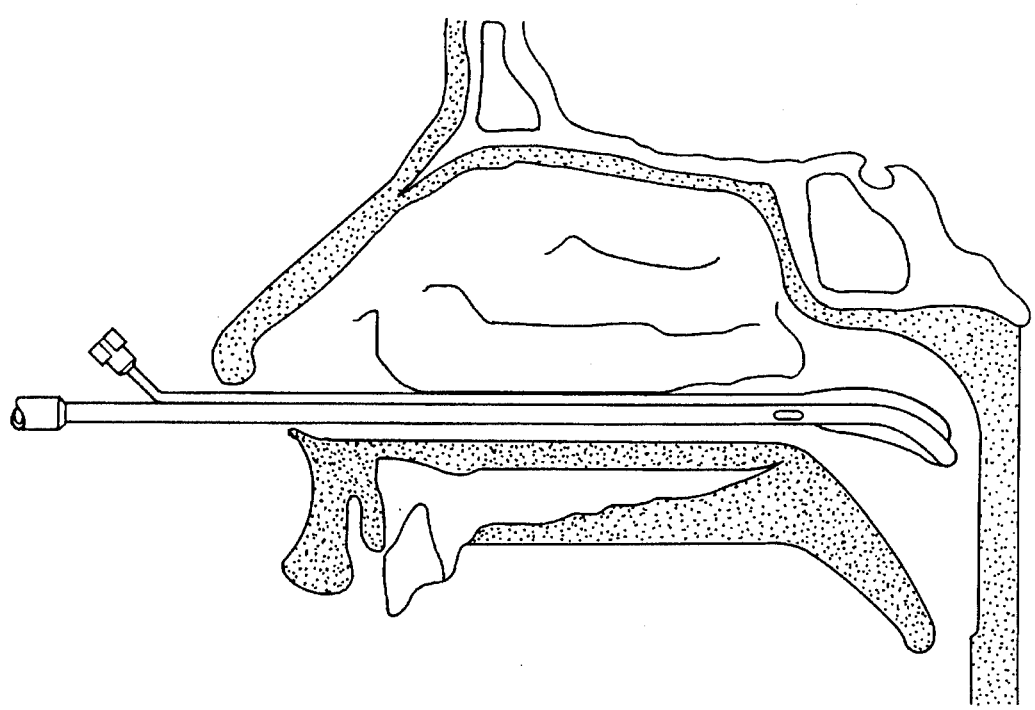
FIG. 5 shows the catheter according to FIG. 1 applied in a nose cavity.
Figure 6:
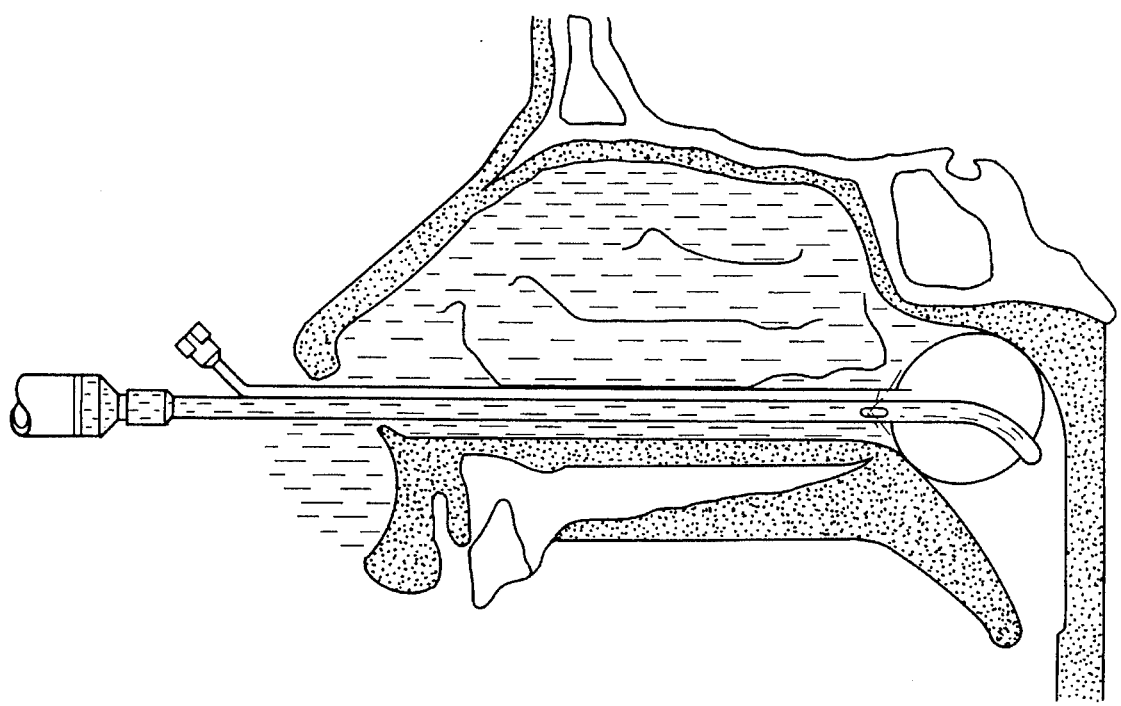
FIG. 6 shows the catheter according to FIG. 1 during administration of warm water.

The nose catheter according to the present invention functions as follows: The patient sits up-eight with his head bent forward. The nose catheter 1 is introduced through the bleeding nose cavity, optionally after spraying with a local anaesthetic (FIG. 5) and is introduced until it has reached the connection of the upper airways at pharynx. The balloon 6 at the front end 5 of the catheter 1 is then filled with air or liquid and becomes inflated until the catheter closes against the rear exit of the nose half part (choanae) (FIG. 6). Using a large syringe 4 (200 ml) applied to the adapter 3 of the catheter 1 warm water or saline solution having a temperature of 48° to 50° C. is administered through the catheter 1. The water is sprayed through the opening 9 of the catheter 1 immediately behind the balloon and rinses thus from the rear through the nose, whereupon it leaves through the nostril.

A theory of the effect of warm water rinse can be based upon the following experimental results. At the rinsing of a rabbit nose using warm water having different temperatures it was determined that rinsing using a water having a temperature of 40° to 46° C. the changes in the nose were minimal, using water having a temperature of 52° to 60° C. tissue damages were discovered, while, when using water having a temperature of 48° to 50° C., such as it has been previously recommended, a pronounced oedema of the mucous membrane was obtained, whereby one can imagine that the damaged mucous membrane between the shell bones in the nose (from which the bleeds most often occur) simple provides a compression of the bleeding area. One could further determine that there was provided a maximal dilatation of the blood vessels of the mucous membrane (up to 10 times the normal diameter). By means of such a dilatation the flow rates decrease as well as the pressure in the vessels, whereby the possibility of a coagulation increases.

At the rinse of the nose cavity it is further obtained that blood clots are washed away from the nose cavity which is positive as clots of dried blood may inhibit the natural healing with connective tissue. Further the hospitalization time is reduced from 4 days to 1 day; immediately after treatment the patient can breath freely through the nose; complications of tamponing are avoided; wash water is hindered to reach the pharynx and the lungs; the treatment need no co-operation with the patient to reach an adequate performance.

I claim:

1. A method for treating a nosebleed, which comprises:
    (a) inserting a catheter having a front end into a bleeding nose having a bleeding point inside the nose and an air passage above the bleeding point, wherein said front end of said catheter has an inflatable balloon, said catheter having an opening for administering a liquid, wherein said opening is immediately below said inflatable balloon,
    (b) positioning said catheter inside the bleeding nose such that said balloon is positioned above the bleeding point inside the nose,
    (c) inflating said balloon thereby substantially blocking the air passage, wherein said inflated balloon contacts the air passage substantially above the bleeding point, and
    (d) passing a liquid through said opening for administering a liquid for a time sufficient to inhibit a nosebleed.

2. The method for treating a nosebleed according to claim 1, wherein the liquid is an aqueous liquid having a temperature of 48° to 50° C.

3. The method for treating a nosebleed according to claim 2, wherein the liquid is a saline solution.

4. The method for treating a nosebleed according to claim 2, wherein the liquid is water.

\* \* \* \* \*